United States Patent
Finlay

(10) Patent No.: US 8,734,326 B2
(45) Date of Patent: May 27, 2014

(54) ARRANGEMENT FOR MANIPULATING A MEDICAL DEVICE

(75) Inventor: Patrick Finlay, Bucks (GB)

(73) Assignee: Freehand 2010 Limited, Peasmarch, Guildford (GB)

( * ) Notice: Subject to any disclaimer, the term of this patent is extended or adjusted under 35 U.S.C. 154(b) by 1353 days.

(21) Appl. No.: 12/183,740

(22) Filed: Jul. 31, 2008

(65) Prior Publication Data

US 2009/0036740 A1 Feb. 5, 2009

(30) Foreign Application Priority Data

Jul. 31, 2007 (GB) .................................. 0714983.4

(51) Int. Cl.
*A61B 1/00* (2006.01)

(52) U.S. Cl.
USPC ............................. 600/102; 600/146; 600/149

(58) Field of Classification Search
USPC .................. 600/104, 146, 147, 149, 102, 148
See application file for complete search history.

(56) References Cited

U.S. PATENT DOCUMENTS

| | | | |
|---|---|---|---|
| 3,174,600 A * | 3/1965 | Oldberg | 192/58.682 |
| 4,499,895 A * | 2/1985 | Takayama | 600/148 |
| 6,349,245 B1 | 2/2002 | Finlay | |
| 6,451,027 B1 | 9/2002 | Cooper et al. | |
| 2004/0092912 A1 | 5/2004 | Jinno | |
| 2005/0234435 A1 | 10/2005 | Layer | |
| 2007/0142823 A1 | 6/2007 | Prisco et al. | |

FOREIGN PATENT DOCUMENTS

| | | |
|---|---|---|
| WO | WO 2005/122916 | 12/2005 |
| WO | WO 2006/124390 | 11/2006 |
| WO | WO 2007/005555 | 1/2007 |

* cited by examiner

*Primary Examiner* — Alireza Nia
(74) *Attorney, Agent, or Firm* — Wilson Sonsini Goodrich & Rosati

(57) ABSTRACT

An arrangement for manipulating a medical device is inserted into the body of a patient. There is a drive element to be driven by a motor. There is also a control element for controlling at least one motion of the medical device. A transmission arrangement transmits motion from the drive element to the control element, the transmission arrangement having first and second members which are frictionally engaged with one another so that motion may be transmitted from one to the other. There is a manual manipulation control, which may be grasped by a user to move the medical device manually while the first and second members remain in frictional engagement with one another.

13 Claims, 2 Drawing Sheets

ARRANGEMENT FOR MANIPULATING A MEDICAL DEVICE

CROSS-REFERENCE TO RELATED U.S. APPLICATIONS

Not applicable.

STATEMENT REGARDING FEDERALLY SPONSORED RESEARCH OR DEVELOPMENT

Not applicable.

NAMES OF PARTIES TO A JOINT RESEARCH AGREEMENT

Not applicable.

REFERENCE TO AN APPENDIX SUBMITTED ON COMPACT DISC

Not applicable.

BACKGROUND OF THE INVENTION

1. Field of the Invention

The present invention relates to a manipulator for a medical device. In particular, embodiments of the invention relate to a device and method for the manipulation of an endoscope or laparoscope during a surgical operation.

2. Description of Related Art Including Information Disclosed Under 37 CFR 1.97 and 37 CFR 1.98

There are a number of occasions during which it is necessary to view and work on remote or inaccessible sites. For example, during a surgical operation it is sometimes necessary to operate on organs, which are within the human body.

In the example of a surgical operation, a surgeon may wish to carry out surgery through as small an incision as possible to reduce scarring and trauma to the patient (in addition, small incisions will reduce the risk of infection and can lead to reductions in post-operative recovery times for the patient).

Thus, there is a requirement for imaging devices or cameras, with relatively small external dimensions, which can be maneuvered through small orifices to allow access to remote or inaccessible sites. To this end, endoscopes (including endoscopic cameras) have been developed. Endoscopes usually comprise a length of rigid or flexible tubing containing an optical fiber system and a light delivery system with a light source attached to a distal end of the tube. A lens system is attached to the optical fiber system at the distal end of the tube, while an endoscopic camera is attached to the optical fiber system at the proximal end of the tube. Thus, it is possible for a user to view an object (or remote site), which is at the distal end of the tube through a display device, which attaches to the endoscopic camera. The distal end of the tube may be maneuvered so as to vary the view of the object (or remote site), which is displayed on the display device.

A variety of endoscopes are specifically designed for use in surgery of this type, for example, endoscopes may be used in laparoscopic surgery (carried out upon the abdominal area of a patient), and in such circumstances will generally be referred to as laparoscopes. Of course, the invention is not limited to devices for use in abdominal surgery, but the examples below will be given with reference to laparoscopes.

A laparoscope may comprise a rigid laparoscope, the proximal end of which is attached to a camera and the distal end of which is inserted into a patient's abdomen (often through their umbilicus).

Traditionally, the laparoscope has been held in place by an assistant who moves the device in response to instructions from the surgeon. More recently, a number of mechanized and robotic devices have been developed to hold and maneuver the laparoscope to allow the surgeon to control the camera directly using, for example, voice commands or head movements.

By necessity, controlled movements of a laparoscope are generally rather slow. This allows a surgeon to have fine control over the positioning of the laparoscope, and to train the camera accurately on small features within the body of a patient.

However, the surgeon will often desire to view a part of the patient, which will require a large movement of the laparoscope from its existing position. In such cases, it takes a significant length of time to move the laparoscope to the desired position using the controls provided.

BRIEF SUMMARY OF THE INVENTION

It is an object of the present invention to seek to provide an improved arrangement for manipulating a medical device.

Accordingly, one aspect of the present invention provides an arrangement for manipulating a medical device to be inserted into the body of a patient, the arrangement comprising: a drive element to be driven by a motor; a control element for controlling at least one motion of the medical device; a transmission arrangement for transmitting motion from the drive element to the control element, the transmission arrangement comprising first and second members which are frictionally engaged with one another so that motion may be transmitted from one to the other; and a manual manipulation control, which may be grasped by a user to move the medical device manually while the first and second members remain in frictional engagement with one another and where the control element is driven by the manual movement, substantially none of this motion is transmitted to the drive element.

Advantageously, the strength of the frictional engagement between the first and second members may be adjusted.

Preferably, an adjustment element is provided to adjust the strength of the frictional engagement between the first and second members.

Conveniently, the first member comprises a rotatable shaft and a second member is mounted on the shaft.

Advantageously, the second element is disposed between a pair of components, each of which may exert frictional forces on the second member.

Preferably, at least one of the components is a spring, which bears against a part of the second member.

Conveniently, the force with which the spring bears against the second member may be adjusted.

Advantageously, an adjustment member is provided, whose distance from the second member may be altered, with the spring being provided in compression between the adjustment member and the second member.

Preferably, the first and second members comprise opposing plates that are frictionally engaged with one another.

Conveniently, the second member comprises a belt, which passes around at least a part of the first member.

Advantageously, the first and second members form part of a viscous fluid drive.

Another aspect of the present invention provides a surgical robot incorporating an arrangement according to the above.

Preferably, the surgical robot incorporates a plurality of arrangements according to the above.

A further aspect of the present invention provides a method of manipulating a medical device to be inserted into the body of a patient, the method comprising the steps of: providing a drive element, arranged to be driven by a motor; providing a control element for controlling at least one motion of the medical device; providing a transmission arrangement for transmitting motion from the drive element to the control element, the transmission arrangement comprising first and second members which are frictionally engaged with one another so that motion may be transmitted from one to the other; and providing a manual manipulation control which may be grasped by a user to move the medical device manually while the first and second members remain in frictional engagement with one another. The control element is driven by the manual movement, substantially none of this motion being transmitted to the drive element.

BRIEF DESCRIPTION OF THE SEVERAL VIEWS OF THE DRAWINGS

In order that the present invention may be more readily understood, embodiments thereof will now be described, by way of example.

DETAILED DESCRIPTION OF THE INVENTION

Figure 1:
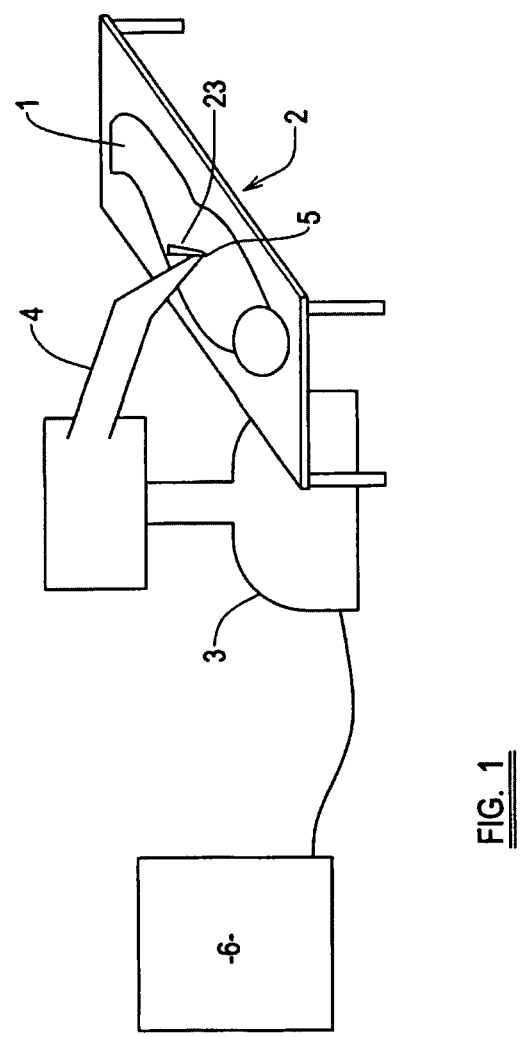
FIG. 1 shows a schematic view of an arrangement embodying the present invention.

Turning firstly to FIG. 1, a patient 1 is shown, lying on a surgical table 2 during the course of a surgical procedure. A surgical robot 3 is provided. The surgical robot 3 stands on the floor of the operating theater close to the operating table 2, and the position of the surgical robot 3 will be registered with respect to the surgical table 2 or with respect to another fixed frame of reference, as will be understood by a person of skill in the art.

The surgical robot 3 has an arm 4 which extends towards the patient 1 and which has a holder (not shown) for holding any one of a variety of surgical instruments, including laparoscopes. Attached to the holder is a laparoscope (not shown), which is inserted into an incision 5 in the abdomen of the patient 1, although it will be appreciated that the invention is not limited to use with laparoscopes.

The surgical robot 3 is controlled through an interface 6, which may comprise a control panel with buttons or a joystick, which may be manipulated by a surgeon to control the movement of the laparoscope within the body of the patient 1. Any suitable method of control may be used, for instance, the monitoring of head movements of a surgeon, or through voice control. Motion of the laparoscope is achieved through one or more motors disposed within the surgical robot 3 or the arm 4 thereof. In one example, a surgeon may be able to control the pan, tilt and zoom of the laparoscope. As discussed above, the motion of the laparoscope when actuated by these motors is relatively slow.

Figure 2:
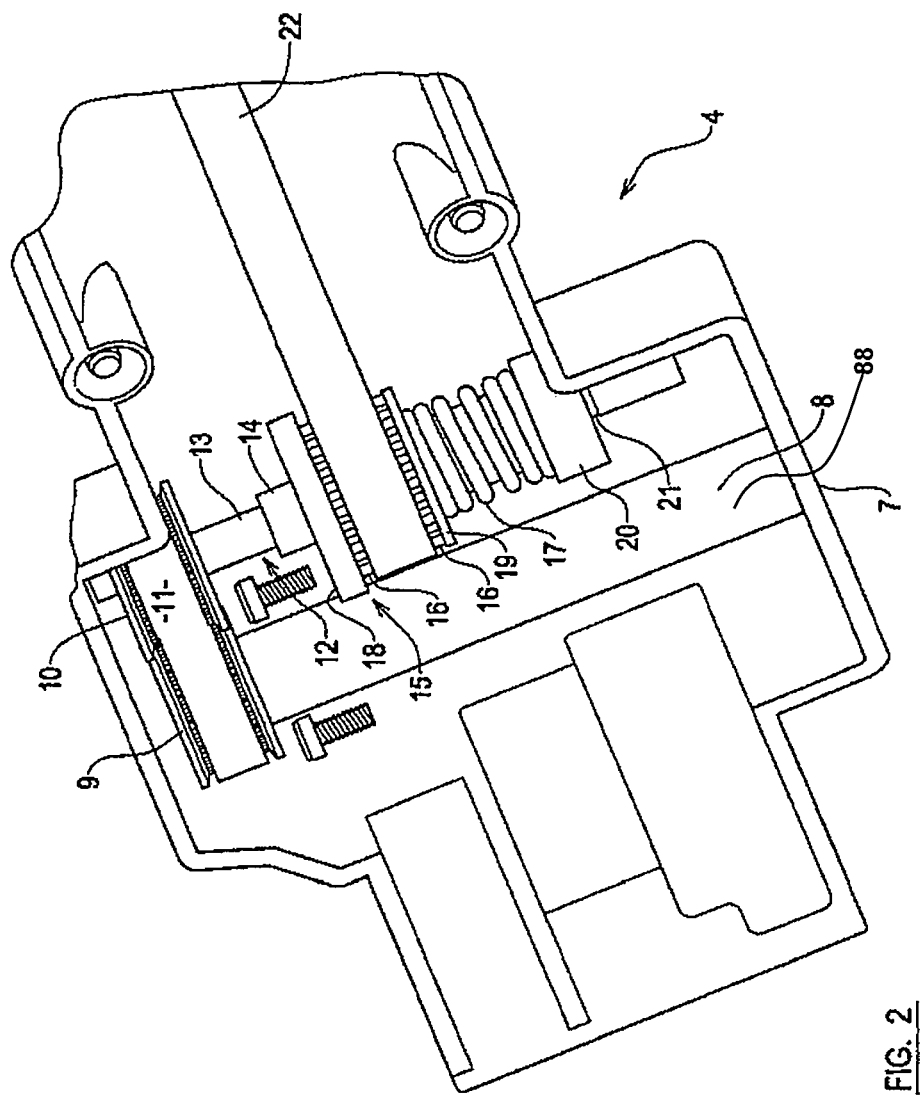
FIG. 2 is a sectional view of part of the arrangement of FIG. 1.

With reference to FIG. 2, a cut-away view of part of the arm 4 of the surgical robot 3 is shown. The arm 4 comprises a housing 7, which is sealed to protect the components within the arm 4.

Within a part of the housing 7, an enclosed motor housing 8 is provided, containing a motor 88. A drive shaft of the motor protrudes from the motor housing and drives rotational motion of a drive wheel 9. A driven wheel 10 is provided adjacent the drive wheel 9, with the drive wheel 9 and driven wheel 10 having axes of rotation which are parallel with each other, but spaced apart. A drive belt 11 passes around the drive wheel 9 and the driven wheel 10. The outer surfaces of the drive wheel 9 and the driven wheel 10, and the inner surface of the drive belt 11, are formed from appropriate materials so that large amounts of friction will be generated between these components. As the drive wheel 9 turns, therefore, rotational motion will be transmitted via the drive belt 11 to the driven wheel 10 with little or no slippage.

The driven wheel 10 is rotationally connected to a main shaft 12, which passes through the rotational axis of the driven wheel 10, and is constrained to rotate therewith, for instance by the provision of a key on the appropriate part of the main shaft 12 and a corresponding keyway in an aperture passing through the centre of the driven wheel 10.

A first part 13 of the main shaft 12 immediately adjacent the driven wheel 10 has a first thickness, and a collar 14 having a greater thickness is provided on the main shaft 12 at a short distance from the driven wheel 10. The collar 14 may be formed integrally with the main shaft 12, or may be fixed thereto by any convenient method, such as welding. However, it is important that the collar 14 may not move either axially or rotationally with respect to the main shaft 12. A first disc 18 is provided adjacent the collar 14, on the side furthest from the driven wheel 10. The first disc 18 is coaxial with the main shaft 12 and is wider than the collar 14. The first disc 18 may be fixed with respect to the main shaft 12 or may be allowed to rotate with respect thereto.

A control driving wheel 15 is provided, having a drum-like configuration with a substantially circular hole passing through the central axis thereof, and with both outer side surfaces 16 being abrasive or otherwise configured to provide grip when placed against another surface. The outer circumferential surface of the control driving wheel 15 is toothed. The control driving wheel 15 is threaded onto the main shaft 12, which is slightly smaller than the hole passing through the centre of the control driving wheel 15, so that the control driving wheel 15 may rotate with respect to the main shaft 12. The control driving wheel 15 is positioned on the main shaft 12 so that a first side surface 16 thereof is abutted against a side of the first disc 18, and the radius of the control driving wheel 15 is slightly less than that of the first disc 18.

A second disc 19 is provided adjacent a second side surface 16 of the control driving wheel 15. The second disc 19 has similar radius to the control driving wheel 15, and may slide axially along the main shaft 12 and rotate with respect thereto. A compression spring 17 is provided on the main shaft 12, so that one end of the compression spring 7 presses against the end of the second disc 19 that is not adjacent the control driving wheel 15.

A nut 20 is threaded onto a threaded portion 21 of the main shaft 12, so that one side of the nut 20 presses against the end of the compression spring 17 that is not in contact with the second disc 19. The nut 20 is advanced along the threaded portion 21 of the main shaft 12 so that the compression spring 17 is under tension, exerting forces both against the second disc 19 and the nut 20. The inner surfaces of the first and second discs 18,19 are abrasive or otherwise formed from a material that is likely to grip against other surfaces.

The main shaft 12 is fixed in position at or near both ends with bearings, so that its position with respect to the housing 7 of the arm 4 is fixed, but the main shaft 12 may nevertheless rotate with respect to the housing 4.

A control drive belt 22, having a toothed inner surface with teeth adapted to cooperate with those of the control driving wheel 15, passes around the outer surface of the control driving wheel 15, and the control driving belt 22 also passes around a part of a rotatable component (not shown), rotation of which causes motion of the laparoscope. The result is that rotation of the control driving wheel 15 will drive the control drive belt 22, which will control at least one aspect of the motion of the laparoscope. This motion could be, for example, any one of a pan, tilt or zoom action, as will be readily understood by a person of skill in the art. In preferred embodiments of the invention, the motion is a zoom motion of the laparoscope, and the amount by which the laparoscope is advanced into the body of the patient 1 will therefore be controlled.

It is envisaged that a surgical robot may have a plurality of arrangements according to the present invention, one each for some or all of the motions that the robot performs.

Operation of the surgical robot 3 will now be described. In normal fine control of the laparoscope, the drive shaft of the motor, which is contained within the motor housing 8, is controlled by a surgeon to rotate in a certain direction. This causes rotation of the drive wheel 9, and hence of the driven wheel 10 and the main shaft 12. The nut 20 is tightened to such an extent that the control driving wheel 15 is gripped between the collar first and second discs 18,19 sufficiently firmly that the rotational motion of the main shaft 12 will be transmitted to the control driving wheel 15. This will, in turn, drive the control drive belt 22, and cause motion of the laparoscope as desired by the surgeon.

Turning to FIG. 1, a manual control handle 23 is provided, protruding from the arm 4 of the surgical robot 3 near the holder of the arm 4. The manual control handle 23 is connected directly to the laparoscope, or to another component that is constrained to move with the laparoscope, such as the holder.

If a surgeon wishes to move the laparoscope through a relatively large distance, the surgeon can grasp the manual control handle 23 and move the laparoscope manually to a new position.

Returning to FIG. 2, it will be understood that manual movement of the laparoscope in this manner will drive the control drive belt 22. This will, in turn, cause rotation of the control driving wheel 15.

It is envisaged, however, that the motion of the laparoscope, when moved by a surgeon exerting a force on the manual control handle 23, will be significantly faster than the motion of the laparoscope when controlled by the motor 88.

The stiffness of the compression spring 17, and the amount by which the nut 20 is threaded onto a threaded portion 21 of the main shaft 12, are selected so that, during manual control of the laparoscope, the control driving wheel 15 will slip with respect to the main shaft 12. The rotational motion of the control driving wheel 15 will have sufficient torque, that frictional forces between the control driving wheel 15 and the first and second discs 18,19 will be overcome. Thus, the motion of the control driving wheel 15 will not be transmitted to the main shaft 12.

It will be appreciated that this is advantageous since this will prevent "back driving" of the motor. Not only would such back driving make manual movement of the laparoscope significantly more difficult, there would also be a possibility that the motor could be damaged by being forcefully driven at a high rotational rate.

The position and orientation of the laparoscope with respect to the arm 4 of the surgical robot 3 will preferably be tracked during manual motion by one or more joint encoders or other sensors, as will be familiar to those skilled in the art.

Therefore, when the surgeon releases the manual control handle 23, the surgical robot 3 will still have an accurate record of the position of the laparoscope within the body of the patient 1. Fine control of the laparoscope through the surgical robot 3 can then continue.

The present invention is not limited to the arrangement described above. In general, however, at least two members are provided which are in frictional engagement with each other, and motion is transmitted through this frictional engagement when driving occurs through a motor. However, during manual manipulation of the laparoscope or other device held by the surgical robot 3, while the two members remain in engagement with one another, the frictional forces therebetween are overcome and little or no motion is transmitted between these two members during manual manipulation. It is preferred that no clutch is provided to allow decoupling or disengagement of the members from one another during manual manipulation.

Any convenient materials can be used for the surfaces of the members, for instance metal, plastic or organic materials may be used, and nylon is preferred for these purposes. Hook and loop materials such as VELCRO™ also be used. It should also be appreciated that the members need not be in direct physical contact with each other, and non-contact arrangements, such as a viscous fluid drive, may be used. A fluid drive incorporating a waxy material with a high molecular weight will be operable to transmit torque at low relative rotational speeds of the members, but at higher relative speeds the material will shear and torque will not be transmitted.

It will be appreciated that the present invention provides an advantageous arrangement, which is particularly useful for holding a medical device to be inserted into a patient's body, but that will find use in a wide variety of applications.

When used in this specification and claims, the terms, "comprises" and "comprising", and variations thereof mean that the specified features, steps or integers are included. The terms are not to be interpreted to exclude the presence of other features, steps or components.

The features disclosed in the foregoing description, or the following claims, or the accompanying drawings, expressed in their specific forms or in terms of a means for performing the disclosed function, or a method or process for attaining the disclosed result, as appropriate, may, separately, or in any combination of such features, be utilized for realizing the invention in diverse forms thereof.

I claim:

1. An arrangement for manipulating a medical device to be inserted into a body of a patient, the arrangement comprising:
    a drive means driven by a motor;
    a control means for controlling at least one motion of the medical device;
    a transmission arrangement means for transmitting motion from the drive means to the control means, the transmission arrangement means comprising first and second members being frictionally engaged with one another with motion being transmittable from one to another; and
    a manual manipulation control means being graspable by a user to move the medical device manually without activating the motor while the first and second members remain in frictional engagement with one another, wherein said control means is drivable by manual movement through the manual manipulation control such that substantially none of the manual movement is transmitted to the drive means.

2. An arrangement according to claim 1, wherein said frictional engagement between the first and second members has adjustable strength.

3. An arrangement according to claim 2, further comprising:
    an adjustment means to adjust the strength of the frictional engagement between the first and second members.

4. An arrangement according to claim 1, wherein the first member comprises a rotatable shaft and wherein the second member is mounted on the shaft.

5. An arrangement according to claim 4, wherein the second member is disposed between a pair of components, each component exerting frictional forces on the second member.

6. An arrangement according to claim 5, wherein at least one of the components is a spring, bearing against a part of the second member.

7. An arrangement according to claim 6, wherein said spring has an adjustable force bearing against the second member.

8. An arrangement according to claim 7, further comprising:
an adjustment means having a distance from the second member which is alterable, said spring being provided in compression between the adjustment means and the second member.

9. An arrangement according to claim 1, wherein the first and second members comprise opposing plates frictionally engaged with one another.

10. An arrangement according to claim 1, wherein the second member comprises a belt, passing around at least a part of the first member.

11. An arrangement according to claim 1, wherein the first and second members form part of a viscous fluid drive.

12. A surgical robot comprising:
an arrangement means for manipulating a medical device to be inserted into a body of a patient, the arrangement means comprising:
a drive means drivable by a motor;
a control means for controlling at least one motion of the medical device;
a transmission arrangement means for transmitting motion from the drive means to the control means, the transmission arrangement comprising first and second members being frictionally engaged with one another with motion being transmittable from one to another; and
a manual manipulation control means being graspable by a user to move the medical device manually without activating the motor while the first and second members remain in frictional engagement with one another, wherein said control means is drivable by manual movement through the manual manipulation control such that substantially none of the manual movement is transmitted to the drive means.

13. A surgical robot according to claim 12, further comprising:
a plurality of said arrangement means.

* * * * *